United States Patent [19]

Fujii et al.

[11] 4,443,603
[45] Apr. 17, 1984

[54] PIPERAZINE DERIVATIVES, OF AROMATIC ACIDS

[75] Inventors: Setsuro Fujii, Toyonaka; Eizou Hattori, Sakado; Mitsuteru Hirata, Saitama; Koichiro Watanabe; Hiroshi Ishihama, both of Higashi-Murayama, all of Japan

[73] Assignee: Kowa Company Limited, Nagoya, Japan

[21] Appl. No.: 381,443

[22] Filed: May 24, 1982

[30] Foreign Application Priority Data

Jun. 5, 1981 [JP] Japan ................... 56-86569

[51] Int. Cl.³ ............... C07D 403/12; C07D 241/04
[52] U.S. Cl. ................... 544/373; 544/121; 544/357; 544/360; 544/364; 544/399; 544/400
[58] Field of Search ............... 542/429, 430, 431, 436, 542/439, 440; 544/121, 357, 373, 360, 364, 399, 400

[56] References Cited

U.S. PATENT DOCUMENTS 3,228,961  1/1966  Vargha et al. ................ 548/573
3,846,430  11/1974  De Antoni et al. ............. 544/393

FOREIGN PATENT DOCUMENTS 19237  11/1980  European Pat. Off. .
5342  9/1967  France .
1544673  of 1968  France .
1543944  of 1968  France .
2240734  3/1975  France .
2244518  4/1975  France .
2358145  2/1978  France .

OTHER PUBLICATIONS

Chemical Abstracts 180955d, vol. 96, (1982).
Chemical Abstracts 174700j, vol. 94, (1981).

Primary Examiner—Henry R. Jiles
Assistant Examiner—Bernard Dentz
Attorney, Agent, or Firm—Oblon, Fisher, Spivak, McClelland & Maier

[57] ABSTRACT

A piperazine derivartive represented by the following formula:

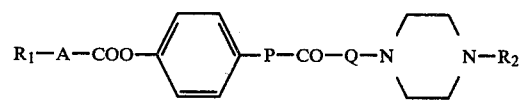

wherein $R_1$: an indolyl group which may optionally be substituted by one or more lower alkyl and/or lower alkoxy groups, naphthyl group which may optionally be saturated partially with 2 or 4 hydrogen atoms, or phenyl or cyclohexyl group which may optionally be substituted by one or more lower alkyl groups;

A: a single bond or alkylene group;

P: a single bond or vinylene group;

Q: an -O-alkylene group or -NH-alkylene group when P is a single bond, or a single bond when P is a vinylene group; and $R_2$: a lower alkyl, morpholino-lower alkyl, morpholinocarbonyl lower alkyl, piperidinocarbonyl lower alkyl, piperazinocarbonyl lower alkyl or lower alkylaminocarbonyl lower alkyl group, or an acid addition salt thereof is a proteolytic enzyme inhibitor.

5 Claims, No Drawings

PIPERAZINE DERIVATIVES, OF AROMATIC ACIDS

BACKGROUND OF THE INVENTION

1. Field of the Invention

This invention relates to novel piperazine derivatives, and more specifically to piperazine derivatives represented by the general formula (I) and their acid addition salts:

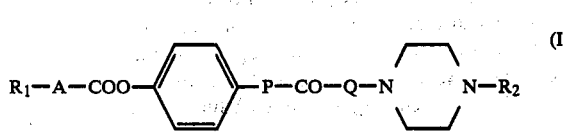

wherein $R_1$: an indolyl group which may optionally be substituted by one or more lower alkyl and/or lower alkoxy groups, naphthyl group which may optionally be saturated partially with 2 or 4 hydrogen atoms, or phenyl or cyclohexyl group which may optionally be substituted by one or more lower alkyl groups;

A: a single bond or alkylene group;

P: a single bond or vinylene group;

Q: an —O—alkylene group or —NH—alkylene group when P is a single bond, or a single bond when P is a vinylene group; and $R_2$: a lower alkyl, morpholino-lower alkyl, morpholinocarbonyl lower alkyl, piperidinocarbonyl lower alkyl, piperazinocarbonyl lower alkyl or lower alkylaminocarbonyl lower alkyl group.

2. Prior Art

The present inventors have synthesized a variety of compounds and have investigated their enzyme inhibitory activities so as to develop proteolytic enzyme inhibitors.

As a result, it has been found that novel piperazine derivatives of the formula (I) above and their acid addition salts have unexpectedly excellent inhibitory effects against chymotrypsin, trypsin and thrombin. This finding has led to the present invention.

SUMMARY OF THE INVENTION

Accordingly, an object of this invention is to provide piperazine derivatives represented by the general formula (I) and their acid addition salts, which are effectively useful as medicines by themselves, in such fields as may depend on the above-mentioned proteolytic enzyme inhibitory effects, for instance, as pharmaceutical products, as formulations with medicines susceptible to deactivation by proteolytic enzymes such as insulin and the like, and as preservatives for foods.

DETAILED DESCRIPTION OF THE PREFERRRED EMBODIMENTS

The present compounds of the formula (I) may be readily prepared, for example, by esterifying 4-substituted phenols of the formula (II) and carboxylic acids of the formula (III) in accordance with the following reaction scheme:

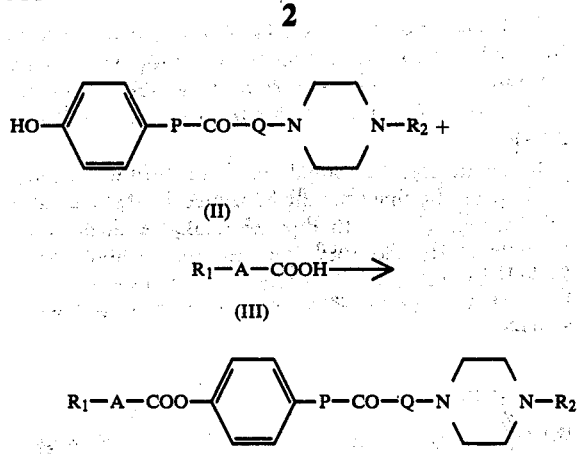

wherein all the symbols have the same significance as defined above.

Existing techniques may be utilized to allow for an esterification reaction between the compounds of the formula (II) and the compounds of the formula (III). For example, the compounds of the formula (I) may be advantageously prepared by reacting reactive derivatives of the compounds of the formula (III), for example, their acid halides, acid anhydrides, mixed acid anhydrides, active esters or azides, with the compounds of the formula (II), or in accordance with an active amide process or an oxidation-reduction process. Alternatively, the compounds of the formula (I) may be produced by reacting the compounds of the formula (II) with the compounds of the formula (III) in the presence of a dehydrating agent such as dicyclohexylcarbodiimide or the like.

The compounds of the formula (III) which may be useful in the invention include conventionally known heterocyclic, aromatic and alicyclic carboxylic acids such as indolycarboxylic acids including indolylacetic acid, naphthylcarboxylic acids, tetrahydronaphthylacetic acids, benzoic acid, cyclohexanecarboxylic acids and the like.

The compounds represented by the formula (II) are novel and may be prepared by reacting benzenecarboxylic acids of the formula (IV) with piperazines of the formula (V) in accordance with the following reaction scheme:

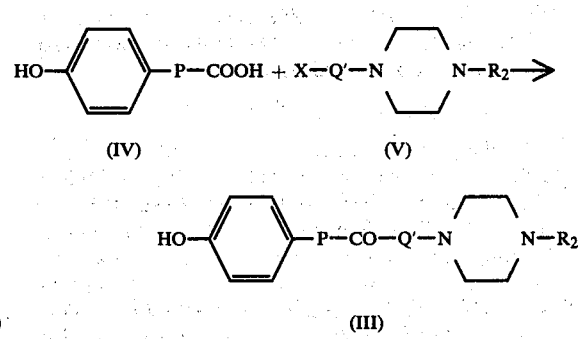

wherein Q' is an alkylene group, X is a halogen atom or a hydroxyl group, and the remaining symbols have the same significance as defined above.

The reaction between the compounds of the formula (IV) and the compounds of the formula (V) is a known esterification reaction and may be carried out in any manner commonly employed in the art.

In this instance, it is desired that, prior to the reaction, the nuclear hydroxyl group of the compounds of the formula (IV) be blocked with a suitable protecting group such for example as an ethoxycarbonyl or benzyl group.

Alternatively, the compounds of the formula (II) may be prepared by first reacting benzenecarboxylic acids of the formula (VI) with piperazinoalkyl amines of the formula (VII) and then reacting the resultant compounds of the formula (VIII) with compounds of the formula (IX) in accordance with the following reaction scheme:

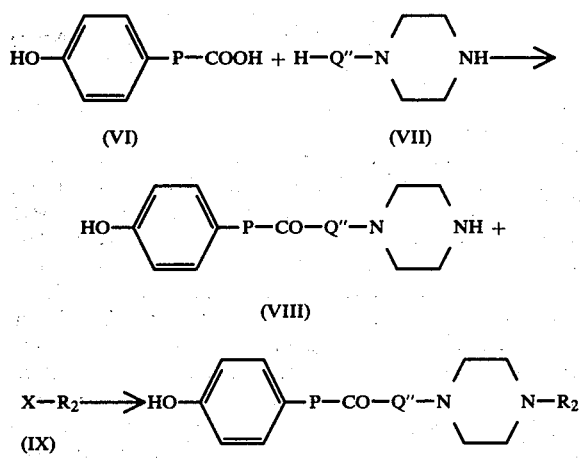

wherein Q" is an —NH—alkylene group, X is a halogen atom, and the remaining symbols have the same significance as defined above.

In this instance, it is likewise desired that, prior to the reactions, the nuclear hydroxyl group of the compounds of the formula (VIII) be blocked with a suitable protecting group such for example as a t-butyl or benzyl group.

The thus prepared compounds of the formula (I) may further be converted by the conventional methods into their inorganic acid salts such as hydrochlorides, sulfates, phosphates and hydrobromates, or their organic acid salts such as acetates, propionates, maleates, fumarates, tartarates, citrates, methanesulfonates, benzenesulfonates and toluene-sulfonates.

The enzyme inhibitory effects of the compounds of the formula (I) according to the invention were tested with the results described hereinafter.

(1) Chymotrypsin Inhibitory Effects

Following the procedure of Muramatsu et al [The Journal of Biochemistry, 62, 408 (1967)], a mixture of 0.1 ml of a dimethylsulfoxide solution of each test compound, 0.1 ml of water and 0.1 ml of a buffer solution containing chymotrypsin in an amount of 10 μg/ml (a 0.1 mole trishydrochloric acid buffer solution, pH 8.0) was incubated for 10 minutes, combined with 0.1 ml of a buffer solution containing 25 millimoles of an ethyl ester of acetyl-L-tyrosine and then reacted with the ethyl ester at 37° C. for 30 minutes. The remaining substrate was caused to develop a color in accordance with the Hestrin method, and the amount was determined by measuring the absorbance at 530 nm. As a control compound, use was made of tosylphenylalanine chloromethyl ketone. The results are shown in Table 1.

(2) Trypsin Inhibitory Effects

Following the procedure of Muramatsu et al [The Journal of Biochemistry, 58, 214 (1967)], a mixture of 0.1 ml of a dimethylsufoxide solution of each test compound, 0.1 ml of a buffer solution (obtained by dissolving 10 millimoles of calcium chloride in a 0.1 mole trishydrochloric acid buffer solution, pH 8.0) and 0.1 ml of a buffer solution containing trypsin in an amount of 2.5 μg/ml was incubated for 10 minutes, mixed with 0.2 ml of a buffer solution containing 25 millimoles of a methyl ester of tosylarginine and then reacted with the methyl ester at 37° C. for 30 minutes. The remaining substrate was caused to develop a color in accordance with the Hestrin method, and the amount was determined by measuring the absorbance at 530 nm. The results are shown in Table 1.

(3) Thrombin Inhibitory Effects

Following the procedure of Tamura et al [Biochim. Biophys. Acta, 484, 417 (1977)], a mixture of 0.1 ml of a dimethylsulfoxide solution of each test compound, 0.1 ml of a buffer solution (a 0.1 mole sodium phosphate buffer, pH 7.4) and 0.1 ml of a buffer solution containing thrombin in an amount of 37.5 units/ml was incubated for 10 minutes, mixed with 0.2 ml of a buffer solution containing 25 millimoles of a methyl ester of tosylarginine and then reacted with the methyl ester at 37° C. for 30 minutes. The remaining substrate was caused to develop a color in accordance with the Hestrin method, and the amount was determined by measuring the absorbance at 530 nm. The results are shown in Table 1.

TABLE 1

| Test Compound | 50% Inhibitory Concentration (mole) | | |
|---|---|---|---|
| | Chymotrypsin | Trypsin | Thrombin |
| 1 | $1 \times 10^{-7}$ | $5 \times 10^{-5}$ | $1 \times 10^{-4}$ |
| 2 | $7 \times 10^{-8}$ | $5 \times 10^{-4}$ | $9 \times 10^{-4}$ |
| 3 | $6 \times 10^{-7}$ | $5 \times 10^{-4}$ | $9 \times 10^{-5}$ |
| 4 | $3 \times 10^{-7}$ | $>10^{-3}$ | $9 \times 10^{-6}$ |
| 5 | $3 \times 10^{-7}$ | $>10^{-3}$ | $9 \times 10^{-6}$ |
| 6 | $5 \times 10^{-7}$ | $8 \times 10^{-5}$ | $6 \times 10^{-5}$ |
| 7 | $6 \times 10^{-7}$ | $2 \times 10^{-4}$ | $7 \times 10^{-5}$ |
| 8 | $5 \times 10^{-8}$ | $>10^{-3}$ | $6 \times 10^{-4}$ |
| 9 | $6 \times 10^{-8}$ | $3 \times 10^{-4}$ | $4 \times 10^{-5}$ |
| 10 | $8 \times 10^{-7}$ | $6 \times 10^{-4}$ | $3 \times 10^{-4}$ |
| 11 | $6 \times 10^{-7}$ | $8 \times 10^{-5}$ | $1 \times 10^{-4}$ |
| TPCK | $5 \times 10^{-4}$ | — | — |

Details of the test compounds are as follows:

1: 4-{[2-[4-[2-(Morpholino)ethyl]piperazino]ethyl]oxycarbonyl}phenyl 5-methoxy-2-methylindole-3-acetate 2: 4-{[2-[4-(Pyrrolidinocarbonylmethyl)piperazino]ethyl]oxycarbonyl}phenyl 1,2-dimethyl-5-methoxyindole-3-acetate 3: 4-{[2-[4-(Morpholinocarbonylmethyl)piperazino]ethyl]oxycarbonyl}phenyl 1,2,3,4-tetrahydro-1-naphthoate 4: 4-{[2-[4-(Dimethylaminocarbonylmethyl)piperazino]ethyl]oxycarbonyl}phenyl 1-naphthylacetate 5: 4-{[2-[4-(Piperidinocarbonylmethyl)piperazino]ethyl]oxycarbonyl}phenyl 1-naphtylacetate 6: 4-{[2-[4-(Dimethylaminocarbonylmethyl)piperazino]ethyl]oxycarbonyl}phenyl 5-methoxy-2-methylindole-3-acetate 7: 4-{[2-[4-(Morpholinocarbonylmethyl)piperazino]ethyl]oxycarbonyl}phenyl 5-methoxy-2-methylindole-3-acetate
8: 4-{[2-[4-(Pyrrolidinocarbonylmethyl)piperazino]ethyl]oxycarbonyl}phenyl 5-methoxyindole-3-acetate
9: 4-{[2-(4-Methylpiperazino)ethyl]oxycarbonyl}phenyl 5-methoxy-2-methylindole-3-acetate
10: 1-[4-(5-Methoxy-2-methylindole-3-acetyloxy)cynnamoyl]-4-(pyrrolidinocarbonylmethyl)piperazine
11: 4-{[2-[4-(Morpholinocarbonylmethyl)piperazino]ethyl]carbamoyl}phenyl 5-methoxy-2-methylindole-3-acetate TPCK: Tosylphenylalanine chloromethyl ketone.

As is clearly evident from the results tabulated in Table 1, the compounds of this invention, which are represented by the general formula (I), have excellent proteolytic enzyme inhibitory effects and are useful as inhibitors against chymotrypsin, trypsin and thrombin.

The above disclosure generally describes the present invention. A more complete understanding will be obtained by the following specific examples which are presented herein for purposes of illustration only and are not construed as limiting to the invention.

EXAMPLE 1
4-{[2-[4-[(Morpholino)ethyl]piperazino]ethyl]oxycarbonyl}phenyl 5-methoxy-2-methylindole-3-acetate (1) In 2 l of benzene was dissolved 623 g of morpholine ethanol. The solution was stirred while maintaining its temperature below 35° C. with ice-cooling, followed by dropwise addition of 735 g of thionyl chloride in 500 ml of benzene. Upon completion of the dropping, the resultant mixture was refluxed with stirring for 4 hours. After cooling, the crystalline precipitate was collected to give 872.4 g (yield: 98.7%) of chloroethylmorpholine hydrochloride having a melting point of 180°–182° C.

In 1 l of toluene were suspended 223 g of the chloroethylmorpholine hydrochloride obtained above, 130 g of piperazine ethanol, 336 ml of triethylamine and 36 g of sodium iodide. The suspension was refluxed with stirring for 2 hours. After cooling, any insoluble matter was removed by filtration. Upon evaporation of the solvent from the resultant filtrate, 209 g of an oily substance was obtained.

The thus obtained oily substance was dissolved together with 161 ml of triethylamine in 1 l of ethyl acetate, followed by dropwise addition with stirring under ice-cooled conditions of 262 g of an acid chloride, which had been prepared from 240 g of p-ethoxycarbonyloxybenzoic acid in a manner commonly known in the art, in 300 ml of ethyl acetate. The resultant mixture was stirred for 3 hours at room temperature. The precipitate was removed by filtration and acidified with 2N-hydrochloric acid. The hydrochloric acid layer was collected, washed with ethyl acetate, neutralized with an aqueous sodium bicarbonate solution and then extracted with chloroform. The chloroform layer was washed with water, dried and concentrated. The resultant crystalline precipitate was recrystallized from a mixed solvent of ethyl acetate and n-hexane, thereby obtaining 329 g (yield: 77.4%) of 2-{4-[2-(morpholino)ethyl]piperazino}ethyl 4-ethoxycarbonyloxybenzoate as colorless crystals having a melting point of 85°–87° C.

Thereafter, the 4-ethoxycarbonyloxybenzoate compound was dissolved in 1.8 l of ethyl acetate, and to the solution was added 64.6 l of pyrrolidine. The resultant mixture was stirred at room temperature for 30 minutes. After the mixture was allowed to stand overnight, the precipitate was collected by filtration and recrystallized from ethanol to give 204 g (yield: 72.6%) of 2-{4-[2-(morpholino)ethyl]piperazino}ethyl 4-hydroxybenzoate as colorless crystals having a melting point of 176°–178° C.

(2) In 3 l of acetonitrile were dissolved 204 g of the 4-hydroxybenzoate obtained in the procedure (1) above, 148 g of 5-methoxy-2-methyl-3-indole acetic acid, 138 g of dicyclohexylcarbodiimide and 8.5 g of 4-dimethylaminopyridine, and the resultant solution was stirred at room temperature for 4 hours. Any precipitated insoluble matter was removed by filtration. The filtrate was concentrated by causing the solvent to evaporate. The residue was taken up in 450 ml of 2N-hydrochloric acid and washed with ethyl acetate. The hydrochloric acid layer was neutralized with sodium bicarbonate and then extracted with chloroform. The chloroform layer was washed with water, dried and concentrated by evaporation of the solvent, thereby obtaining a dark reddish, oily substance.

The substance was dissolved in 3.5 l of a mixed solvent of acetonitrile and ethanol (4:1) and then combined with a stoichiometric amount of a hydrochloric acid/dioxane solution. The resultant mixture was allowed to stand overnight in cold conditions. Upon collecting by filtration and drying the resultant crystals, 294 g (yield: 77.7%) of 4-{[2-[4-[2-(morpholino)ethyl]piperazino]ethyl]oxycarbonyl}phenyl 5-methoxy-2-methylindole-3-acetate tris-hydrochloride was obtained as light yellowish crystals having a melting point of 231°–233° C.

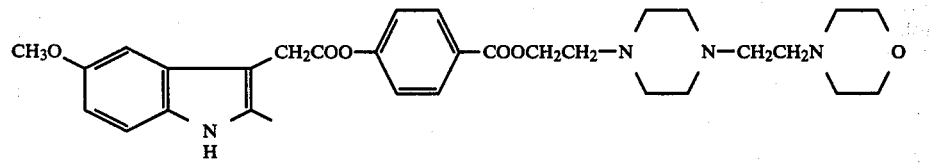

EXAMPLE 2

4-{[2-[4-(Morpholinocarbonylmethyl)piperazino]ethyl]carbamoyl}phenyl 5-methoxy-2-methylindole-3-acetate

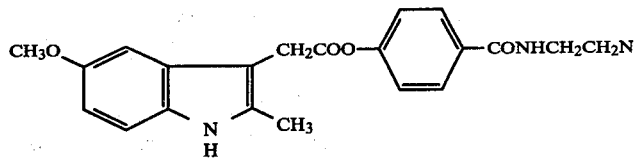

(1) In chloroform were dissolved 25.4 g of phenyl 4-(benzyloxy)benzoate and 21.6 g of N-(2-aminoethyl)-piperazine. The solution was heated and refluxed for 5 hours. After completion of the reaction, the reaction mixture was concectrated under reduced pressure, and the residue was dissolved in ethyl acetate, followed by extraction with 105 ml of 4N-hydrochloric acid. The hydrochloric acid layer was collected, to which 17 g of sodium hydroxide was added with ice-cooling to neutralize the layer. The layer was then extracted with chloroform, washed with brine and dried. The solvent was caused to evaporate, thereby allowing crystals to precipitate. These crystals were recrystallized from a mixed solvent of ethyl acetate and ether, thereby obtaining 8.5 g (yield: 30.0%) of 2-(piperazino)ethyl-4-(benzyloxy)benzamide as colorless crystals having a melting point of 116°–118° C.

A solution of 8.0 g of the thus obtained benzamide, 3.45 g of potassium carbonate and 0.37 g of sodium iodide in 80 ml of ethanol was mixed with 7.72 g of N-(chloroacetyl) morpholine, and the resultant mixture was heated and refluxed for 5 hours. After completion of the reaction, any insoluble matter was removed by filtration. The solvent was evaporated under reduced pressure from the resultant filtrate. The residue was mixed with and dissolved in 90 ml of 1N-hydrochloric acid. The solution was washed with ethyl acetate, neutralized with sodium bicarbonate and then extracted with 500 ml of ethyl acetate. The extract was dried and concentrated under reduced pressure. The residue was subjected to chromatography using a silica gel column and purified with a mixed solvent of chloroform and methanol (10:1), thereby obtaining 5.3 g (yield: 48.1%) of 2-[4-(morpholinocarbonylmethyl)piperazino]ethyl-4-(benzyloxy)benzamide as colorless crystals having a melting point of 149°–151° C.

In 80 ml of methanol was dissolved 5.2 g of the thus obtained benzamide compound, followed by addition of 1 g of 10% palladium carbon. The compound was catalytically reduced for 3 hours at 40° C. and then purified in a manner commonly employed in the art, thereby obtaining 4.18 g (a stoichiometric amount) of N-{2-[4-(morpholinocarbonylmethyl)piperazino]ethyl}4-hydroxybenzamide as an oily substance.

Elementary Analysis:

| | |
|---|---|
| Calculated for C<sub>19</sub>H<sub>28</sub>N<sub>4</sub>O<sub>4</sub> | C 60.62; H 7.50; N 14.88 |
| Found | C 60.34; H 7.41; N 14.70 |

(2) In 30 l of acetonitrile were dissolved 4.18 g of the benzamide compound obtained in the procedure (1) above, 3.65 g of 5-methoxy-2-methylindole-3-acetic acid and 0.2 g of 4-dimethylaminopyridine. To the solution was added 3.43 g of dicyclohexylcarbodiimide, and the mixture was stirred at room temperature for 2 hours. Any insoluble matter was removed by filtration, and the filtrate was concentrated by causing the solvent to evaporate. The residue was taken up in ethyl acetate and thereafter extracted with 20 ml of 2N-hydrochloric acid. The hydrochloric acid layer was collected and, after neutralized with sodium bicarbonate, extracted with ethyl acetate. The extract was washed with water and dried. The solvent was caused to evaporate, and the resultant oily substance was dissolved in acetonitrile. The addition of 1.73 g of maleic acid to the acetonitrile solution gave, as colorless crystals having a melting point of 151°–153.5° C., 5.2 g (yield: 86.3%) of 4-{[2-[4-(morpholinocarbonylmethyl)piperazino]ethyl]carbamoyl}phenyl 5-methoxy-2-methylindole-3-acetate bis-maleate.

EXAMPLE 3

1-(Pyrrolidinocarbonylmethyl)-4-[4-(1,2,3,4-tetrahydro-1-naphthoyloxy)cinnamoyl]piperazine

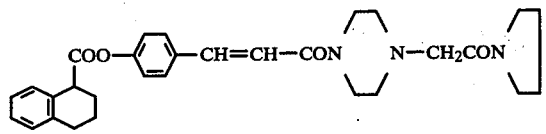

(1) In 140 ml of chloroform were dissolved 17.7 g of 1-(pyrrolidinocarbonylmethyl)piperazine and 8.4 ml of triethylamine. To the solution was added 15.2 g of 4-(ethoxycarbonyloxy)cinnamoylchloride with ice-cooling, followed by stirring the resultant mixture overnight at room temperature. After completion of the reaction, the reaction mixture was concentrated under reduced pressure and dissolved in ethyl acetate. Any insoluble matter was removed by filtration, and the filtrate was extracted with 140 ml of 1N-hydrochloric acid. The extract was washed with ethyl acetate, neutralized with sodium bicarbonate and then extracted with chloroform. The chloroform layer was successively washed with water and then with brine. The layer was then dried and subjected to distillation to remove the solvent. The resultant crystals were recrystallized from ethyl acetate, thereby obtaining 13.4 g (yield: 54.0%) of 1-[4-(ethoxycarbonyloxy)cinnamoyl]-4-(pyrrolidinocarbonylmethyl)piperazine as crystals having a melting point of 128°–130° C.

The piperazine compound was dissolved in 150 ml of chloroform, and to the solution was added 2.30 g of pyrrolidine. The resultant mixture was stirred at room temperature for 1.5 hours. After completion of the reaction, the solvent was evaporated, and the residue was subjected to chromatography using a silica gel column and purified with a mixed solvent of chloroform and methanol (10:1), thereby obtaining 11.1 g (a stoichiometric amount) of 1-(4-hydroxycinnamoyl)-4-(pyrrolidinocarbonylmethyl)piperazine as a colorless oily substance.

Elementary Analysis:

| | |
|---|---|
| Calculated for $C_{19}H_{25}N_3O_3$ | C 66.45; H 7.34; N 12.24 |
| Found | C 66.24; H 7.28; N 12.09 |

(2) Using the 1-(4-hydroxycinnamoyl)4-(pyrrolidinocarbonylmethyl)piperazine obtained in the procedure (1) above and 1,2,3,4-tetrahydro-1-naphthoylchloride, the procedure (2) of Example 1 was followed to give 1-(pyrrolidinocarbonylmethyl-4-(1,2,3,4-tetrahydro-1-naphthoyloxy)cinnamoyl piperazine hydrochloride as crystals having a melting point of 237.5°-240.5° C. (yield: 49.5%).

EXAMPLES 4-25

The following compounds were prepared by the same procedures as in Examples 1 to 3.

4-{[2-[4-(Morpholinocarbonylmethyl)piperazino]ethyl]carbamoyl}phenyl naphthyl-1-acetate bis-hydrochloride (melting point: 230°-232° C.)

4-{[2-[4-(Piperidinocarbonylmethyl)piperazino]ethyl]oxycarbonyl}phenyl 1,2-dimethyl-5-methoxyindole-3-acetate bis-hydrochloride (melting point: 225°-226° C.)

4-{[2-[4-[2-(Morpholino)ethyl]piperazino]ethyl]oxycarbonyl}phenyl 1,2-dimethyl-5-methoxyindole-3-acetate tris-hydrochloride (melting point: 227°-229° C.)

4-{[2-[4-(Morpholinocarbonylmethyl)piperazino]ethyl]oxycarbonyl}phenyl 1,2-dimethyl-5-methoxyindole-3-acetate bis-hydrochloride (melting point: 219°-221° C.)

4-{[2-[4-(Pyrrolidinocarbonylmethyl)piperazino]ethyl]oxycarbonyl}phenyl 1,2-dimethyl-5-methoxyindole-3-acetate bis-hydrochloride (melting point: 218°-219° C.)

4-{[2-[4-(Piperidinocarbonylmethyl)piperazino]ethyl]oxycarbonyl}phenyl 5-methoxy-2-methylindole-3-acetate bis-hydrochloride (melting point: 215°-217° C.)

4-{[2-[4-(Morpholinocarbonylmethyl)piperazino]ethyl]oxycarbonyl}phenyl 5-methoxy-2-methylindole-3-acetate bis-hydrochloride (melting point: 217°-219° C.)

4-{[2-[4-(Pyrrolidinocarbonylmethyl)piperazino]ethyl]oxycarbonyl}phenyl 5-methoxy-2-methylindole-3-acetate bis-hydrochloride (melting point: 223°-225.5° C.)

4-{[2-[4-(Dimethylaminocarbonylmethyl)piperazino]ethyl]oxycarbonyl}phenyl 1,2-dimethyl-5-methoxyindole-3-acetate bis-hydrochloride (melting point: 224°-226° C.)

4-{[2-[4-)Pyrrolidinocarbonylmethyl)piperazino]ethyl]oxycarbonyl}phenyl 5-methoxyindole-3-acetate (melting point: 124.5°-128.5° C.) and its bis-hydrochloride (melting point: 229°-235.5° C.)

4-{[2-[4-(Dimethylaminocarbonylmethyl)piperazino]ethyl]oxycarbonyl}phenyl 5-methoxy-2-methylindole-3-acetate bis-hydrochloride (melting point: 229°-230° C.)

4-{[2-[4-(Morpholinocarbonylmethyl)piperazino]ethyl]oxycarbonyl}phenyl 4-methylbenzoate bis-hydrochloride (melting point: 233°-235° C.)

4-{[2-[4-(Morpholinocarbonylmethyl)piperazino]ethyl]oxycarbonyl}phenyl cyclohexylcarboxylate bis-hydrochloride (melting point: 229°-230° C.)

4-{[2-[4-(Morpholinocarbonylmethyl)piperazino]ethyl]oxycarbonyl}phenyl benzoate bis-hydrochloride (melting point: 232°-234° C.)

4-{[2-[4-(Dimethylaminocarbonylmethyl)piperazino]ethyl]oxycarbonyl}phenyl 1-naphthylacetate bis-hydrochloride (melting point: 200°-202.5° C.)

4-{[2-[4-(Morpholinocarbonylmethyl)piperazino]ethyl]oxycarbonyl}phenyl 1,2,3,4-tetrahydro-1-naphthoate bis-hydrochloride (melting point: 222°-224° C.)

4-{[2-[4-(Pyrrolidinocarbonylmethyl)piperazino]ethyl]oxycarbonyl}phenyl 1-naphthylacetate bis-hydrochloride (melting point: 223°-226° C.)

4-{[2-[4-(Morpholinocarbonylmethyl)piperazino]ethyl]oxycarbonyl}phenyl 1-naphthylacetate bis-hydrochloride (melting point: 217°-221° C.)

4-{[2-[4-(Piperidinocarbonylmethyl)piperazino]ethyl]oxycarbonyl}phenyl 1-naphthylacetate bis-hydrochloride (melting point: 209°-213.5° C.)

4-{[2-(4-Methylpiperazino)ethyl]oxycarbonyl}phenyl 5-methoxy-2-methylindole-3-acetate bis-hydrochloride (melting point: 228°-230° C.)

4-{[2-(4-Methylpiperazino)ethyl]oxycarbonyl}phenyl 5-methoxyindole-3-acetate bis-hydrochloride (melting point: 78°-81° C.)

1-[4-(5-Methoxy-2-methylindole-3-acetyloxy)cinnamoyl]-4-(pyrrolidinocarbonylmethyl)piperazine (obtained in powder form).

This invention now being fully described, it is apparent to those versed in the art that many changes and modifications can be made to the invention without departing the spirit or scope of the invention set forth herein.

What is claimed is:

1. A piperazine derivative represented by the following formula:

$$R_1-A-COO-\underset{}{\underbrace{\bigcirc}}-P-CO-Q-N\underset{}{\underbrace{\bigcirc}}N-R_2$$

wherein $R_1$: an indolyl group which may optionally be substituted by one or more lower alkyl and/or lower alkoxy groups, naphthyl group which may optionally be saturated partially with 2 or 4 hydrogen atoms, or phenyl or cyclohexyl group which may optionally be substituted by one or more lower alkyl groups;

A: a single bond or lower alkylene group;

P: a single bond or vinylene group;

Q: an —O—lower alkylene group or —NH—lower alkylene group when P is a single bond, or a single bond when P is a vinylene group; and $R_2$: a lower alkyl, morpholino-lower alkyl, morpholinocarbonyl lower alkyl, piperidinocarbonyl lower alkyl, piperazinocarbonyl lower alkyl or lower alkylaminocarbonyl lower alkyl group, or a pharmaceutically acceptable acid addition salt thereof.

2. The piperazine derivative of claim 1 wherein $R_1$: an indolyl group substituted by one or more lower alkyl groups, or an indolyl group substituted by one or more lower alkoxy groups.

3. The piperazine derivative of claim 1 wherein A: methylene.

4. The piperazine derivative of claim 1 wherein Q: an —O—ethylene or —NH—ethylene.

5. The piperazine derivative of claim 1 wherein A: methylene and Q: an —O—ethylene or —NH—ethylene.

* * * * *